(12) United States Patent
Smith et al.

(10) Patent No.: US 7,932,293 B2
(45) Date of Patent: Apr. 26, 2011

(54) ALDEHYDE COMPOSITIONS AND METHODS FOR PROVIDING FRAGRANCE CONTAINING THE SAME

(75) Inventors: Catherine Marie Smith, Bayville, NJ (US); Richard M. Boden, Ocean, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 297 days.

(21) Appl. No.: 11/765,723

(22) Filed: Jun. 20, 2007

(65) Prior Publication Data

US 2008/0319088 A1    Dec. 25, 2008

(51) Int. Cl.
*A61K 8/33* (2006.01)
*C07C 47/02* (2006.01)

(52) U.S. Cl. ................ 514/693; 510/101; 538/496
(58) Field of Classification Search ................ None
See application file for complete search history.

(56) References Cited

U.S. PATENT DOCUMENTS

| | | | |
|---|---|---|---|
| 2,148,437 A | | 2/1939 | Coleman et al. |
| 2,153,513 A | | 4/1939 | Coleman et al. |
| 2,241,421 A | | 5/1941 | Price et al. |
| 4,532,364 A | * | 7/1985 | Fujioka et al. ........... 568/444 |

FOREIGN PATENT DOCUMENTS

JP    61-134337    6/1986

OTHER PUBLICATIONS

Williams et al., "Total Synthesis of (-)-Stemonine", Org. Lett., 2003, 5(18), pp. 3361-3364.*

* cited by examiner

*Primary Examiner* — Frederick Krass
*Assistant Examiner* — Brian Gulledge
(74) *Attorney, Agent, or Firm* — Elizabeth M. Quirk; XuFan Tseng; Joseph F. Leightner

(57) ABSTRACT

The present invention is directed to the novel aldehyde compounds, represented by the general structure of Formula I set forth below:

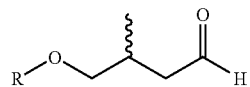

Formula I wherein R is a straight, branched hydrocarbon moiety consisting of 3 to 10 carbon atoms and may contain one or more oxygen heteroatom.

3 Claims, No Drawings

ALDEHYDE COMPOSITIONS AND METHODS FOR PROVIDING FRAGRANCE CONTAINING THE SAME

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

One embodiment is directed to the novel aldehyde compounds, represented by the general structure of Formula I set forth below:

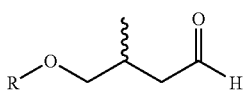

Formula I wherein R is a straight, branched hydrocarbon moiety consisting of 3 to 10 carbon atoms and may contain one or more oxygen heteroatom.

DETAILED DESCRIPTION OF THE INVENTION

In Formulae I above, R represent a straight or branched hydrocarbon moiety consisting of less than 10 and may contain one or more oxygen heteroatom. Suitable straight hydrocarbon moieties include propyl, butyl, pentyl, hexyl, and the like. Suitable branched hydrocarbon moieties include isopropyl, sec-butyl, tert-butyl, 2-ethyl-propyl, and the like. Suitable hydrocarbon moieties containing double bonds include prenyl, 3-Hexene, 2,4-hexadiene and the like.

According to one embodiment of the invention, the following are preferred compounds of the present invention:

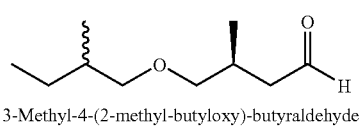

3-Methyl-4-(2-methyl-butyloxy)-butyraldehyde (I)

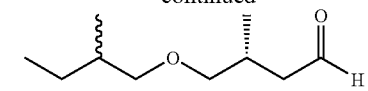

(II)

3-Methyl-4-pentyloxy-butyraldehyde

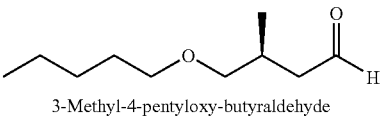

(III)

3-methyl-4-Hexyloxy-butyraldehyde

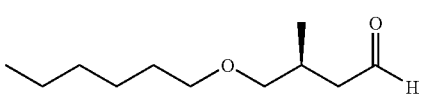

(IV)

3-methyl-4-Heptyloxy-butyraldehyde

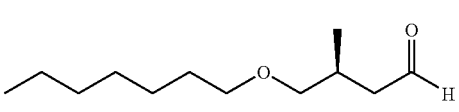

(V)

3-Methyl-4-(1-methyl-hexyloxy)-butyraldehyde

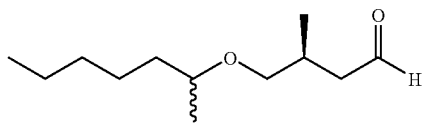

(VI)

3-Methyl-4-octyloxy-butyraldehyde

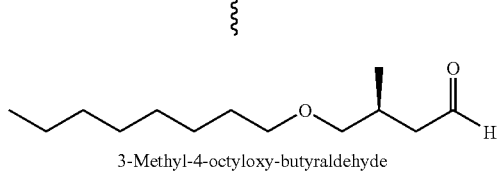

(VII)

3-Methyl-4-(3- methyl-3-methoxy-butyloxy)-butyraldehyde

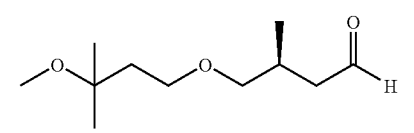

Structure I possesses citrus, floral, citronellal, and green notes; Structure II possesses dusty, metallic, and aldehydic notes; Structure III possesses aldehydic, mandarin aldehyde, citrus peel, fruity, floral, and green; Structure IV has aldehydic, citrus, orange, tangy, juicy, and zesty notes; Structure V possesses aldehydic, citrus, lactonic, green and creamy;

Structure VI possesses aldehydic, fatty and citrus notes; and Structure VII possesses aldehydic, fatty and citrus notes.

The compounds of the present invention may contain one or more chiral centers and as such they may exist as a mixture of enantiomers and diastereomers, or they may be resolved as enantiomerically and diastereomerically pure forms. However, resolving stereoisomers adds to the complexity of manufacture and purification of these compounds and so it is preferred to use the compounds as mixtures of their stereoisomers simply for economic reasons. However, if it is desired to prepare pure stereoisomers, this may be achieved according to methodology known in the art.

According to the present invention, the aldehydes are synthesized via a two step process. The starting alcohol is first reacted with 3-chloro-2-methylpropene, also commonly known as methallyl chloride, to generate the ether intermediates. These alcohols range in chain length from about 3 to about 10 carbons and may either be linear or branched.

The second step consists of performing a hydroformylation or "oxo" reaction. The reaction occurs at the terminal end of the double bond to generate the aldehyde product shown as the major product.

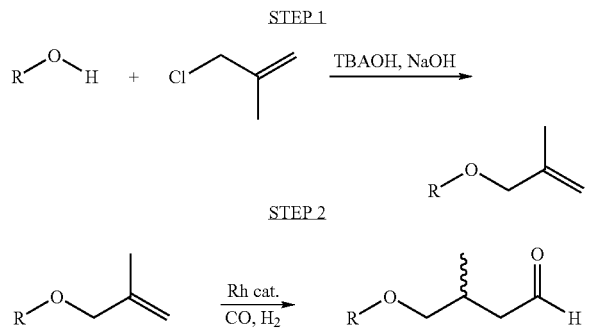

The starting materials for the ether formation selected from 2-methyl-1-butanol, 1-pentanol, 1-hexanol, 1-heptanol, 1-octanol, 3-methoxy-3-methyl-1-butanol, tetrabutylammonium hydroxide, sodium hydroxide, and 3-chloro-2-propene are commercially availably from Aldrich Chemical Company. The material 2-heptanol is commercially available from International Flavors & Fragrances Inc.

The materials used in the Hydroformylation (oxo) reaction are Wilkinson's Catalyst which is chlorotris(triphenylphosphine)rhodium(I) and is commercially available from Johnson Matthey, carbon dioxide, hydrogen, and methanol which are commercially available from Aldrich Chemical Company.

The use of the compounds of the present invention are widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. All U.S. patents mentioned above are incorporated herein by reference. IFF as used in the examples is understood to mean International Flavors & Fragrances Inc., New York, N.Y., USA. All fragrance materials mentioned in the examples are available from IFF.

Example I

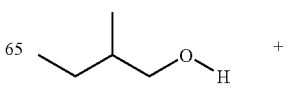

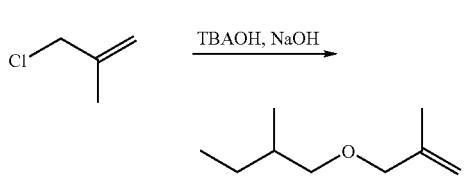

1-(2-methyl-allyloxy)-2-methylbutane: In a 3000 mL reaction flask was charged 2-methyl-1-butanol (440 g, 5.0 mol), a 40% by weight in water solution of tetrabutyl ammonium hydroxide (100 g, 0.15 mol), and a 50% by weight solution of NaOH (488 g, 6.1 mol). The mixture was heated to 70° C. and 3-chloro-2-propene (550 g, 6.1 mol) was fed into the reaction over 3 hours. The reaction was aged for 7 hours at 70° C., then cooled to room temperature. The reaction was quenched with 600 mL of water, and the layers separated. The organic layer washed with 600 mL water and 600 mL of brine. The crude product was purified by distillation to give 482 g of ether, a 68% yield.

1-(2-methyl-allyloxy)-2-methylbutane: $^1$H NMR (500 MHz, CDCl$_3$) δ 4.95 (s, 1H), 4.87 (s, 1H), 3.86 (s, 2H), 3.28-3.23 (m, 1H), 3.19-3.15 (m, 1H) 1.73 (s, 3H), 1.69-1.61 (m, 1H), 1.51-1.42 (m, 1H), 1.19-1.10 (m, 1H), 0.92-0.88 (m, 6H).

The compound possesses floral, green, spicy, leafy notes.

Example II

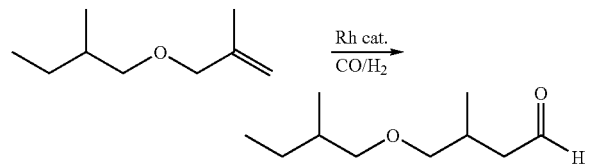

3-Methyl-4-(2-methyl-butyloxy)-butyraldehyde (I): To an autoclave was charged Wilkinson's Catalyst catalyst (5.8 g, 6.3 mmol) and 1-(2-methyl-allyloxy)-2-methylbutane (450 g, 3.1 mol). The reaction was pressurized to 300 psig with CO/H$_2$, and heated to 110° C. for 5 hours. The reaction was then cooled and returned to atmospheric pressure. The crude material was first rushed over, and then fractionally distilled to yield 328 g of aldehyde 62% yield.

3-Methyl-4-(2-methyl-butyloxy)-butyraldehyde (I): $^1$H NMR (500 MHz, CDCl$_3$) δ 9.76 (t, J=2.02 Hz, 1H), 3.37-3.31 (m, 1H), 3.28-3.21 (m, 1H), 3.20-3.11 (m, 2H), 2.54-2.47 (ddd, J=16.02, 6.39, 2.11 Hz, 1H), 2.37 (octet, J=6.52 Hz, 1H) 2.29-2.22 (ddd, J=15.77, 6.56, 1.64 Hz, 1H), 1.65-1.56 (octet, J=6.55 Hz, 1H), 1.45-1.37 (m, 1H), 1.17-1.07 (m, 1H), 0.97 (d, J=6.80 Hz, 3H), 0.88 (t, J=7.39 Hz, 3H), 0.87 (d, J=6.92 Hz, 3H).

The compound possesses citrus, floral citronellal, and green notes.

Example III

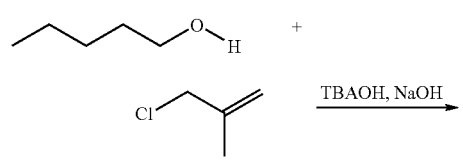

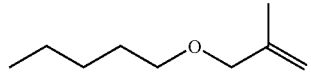

1-(2-methyl-allyloxy)-pentane: In a 3000 mL reaction flask was charged 1-pentanol (400 g, 4.5 mol), a 40% by weight in water solution of tetrabutyl ammonium hydroxide (100 g, 0.15 mol), and a 50% by weight solution of NaOH (435 g, 5.4 mol). The mixture was heated to 70° C. and 3-chloro-2-propene (486 g, 5.4 mol) was fed into the reaction over 3 hours. The reaction was aged for 7 hours at 70° C., then cooled to room temperature. The reaction was quenched with 600 mL of water, and the layers separated. The organic layer washed with 600 mL water and 600 mL of brine. The crude product was purified by distillation to give 435 g of ether, a 68% yield.

1-(2-methyl-allyloxy)-pentane: $^1$H NMR (500 MHz, CDCl$_3$) δ 4.95 (s, 1H), 4.87 (s, 1H), 3.86 (s, 2H), 3.39 (t, J=6.64 Hz, 2H), 1.73 (s, 3H), 1.59 (t, J=6.86 Hz, 2H), 1.34 (m, 4H), 0.90 (t, J=6.82 Hz, 3H).

The compound possesses metallic and green notes.

Example IV

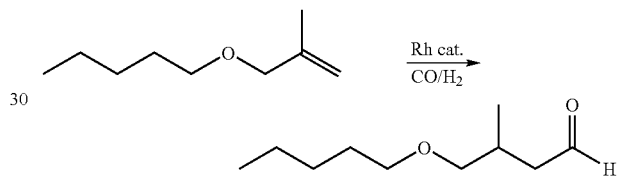

3-Methyl-4-pentyloxy-butyraldehyde (II): To an autoclave was charged Wilkinson's Catalyst catalyst (5.5 g, 5.9 mmol) and 1-(2-methyl-allyloxy)-pentane (420 g, 2.9 mol). The reaction was pressurized to 300 psig with CO/H$_2$, and heated to 110° C. for 5 hours. The reaction was then cooled and returned to atmospheric pressure. The crude material was first rushed over, and then fractionally distilled to yield 332 g of aldehyde 66% yield.

3-Methyl-4-pentyloxy-butyraldehyde (II): $^1$H NMR (500 MHz, CDCl$_3$) δ 9.76 (t, J=2.23 Hz, 1H), 3.40-3.34 (m, 3H), 3.17 (dd, J=9.23, 7.83 Hz, 1H), 2.51 (ddd, J=16.02, 6.38, 2.35 Hz, 1H), 2.37 (octet, J=6.46 Hz, 1H), 2.25 (ddd, J=16.02, 6.99, 2.13 Hz, 1H), 1.54 (p, J=7.08 Hz, 2H), 1.31 (m, 4H), 0.97 (d, J=6.80 Hz, 3H), 0.90 (t, J=6.97 Hz, 3H).

The compound possesses dusty, metallic, and aldehydic notes.

Example V

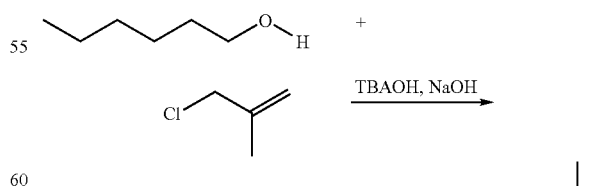

1-(2-methyl-allyloxy)-hexane: In a 3000 mL reaction flask was charged 1-hexanol (500 g, 4.9 mol), a 40% by weight in water solution of tetrabutyl ammonium hydroxide (65 g, 0.10 mol), and a 50% by weight solution of NaOH (480 g, 6.6 mol). The mixture was heated to 70° C. and 3-chloro-2-propene (530 g, 5.9 mol) was fed into the reaction over 3 hours. The reaction was aged for 7 hours at 70° C., and then cooled to room temperature. The reaction was quenched with 800 mL of water, and the layers separated. The organic layer washed with 800 mL water and 800 mL of brine. The crude product was purified by distillation to give 550 g of ether, a 72% yield.

1-(2-methyl-allyloxy)-hexane: $^1$H NMR (500 MHz, CDCl$_3$) δ 4.95 (s, 1H), 4.87 (s, 1H), 3.86 (s, 2H), 3.39 (t, J=6.65 Hz, 2H), 1.73 (s, 3H), 1.58 (p, J=7.34 Hz, 2H), 1.38-1.27 (m, 6H), 0.89 (t, J=6.80 Hz, 3H).

The compound possesses metallic and green notes.

Example VI

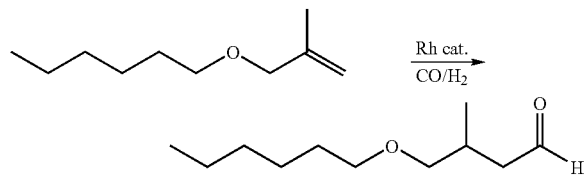

3-methyl-4-hexyloxy-butyraldehyde (III): To an autoclave was charged Wilkinson's Catalyst catalyst (6.3 g, 6.8 mmol) and 1-(2-methyl-allyloxy)-hexane (530 g, 3.4 mol). The reaction was pressurized to 300 psig with CO/H$_2$, and heated to 110° C. for 5 hours. The reaction was then cooled and returned to atmospheric pressure. The crude material was first rushed over, and then fractionally distilled to yield 407 g of aldehyde 64% yield.

3-methyl-4-hexyloxy-butyraldehyde (III): $^1$H NMR (500 MHz, CDCl$_3$) δ 9.76 (t, J=2.2 Hz, 1H), 3.42-3.34 (m, 3H), 3.17 (dd, J=9.2, 7.9 Hz, 1H), 2.51 (ddd, J=16.0, 6.4, 2.4 Hz, 1H), 2.36 (octet, J=6.6 Hz, 1H), 2.25 (ddd, J=16.0, 6.9, 2.1 Hz, 1H), 1.53 (p, J=6.7 Hz, 2H), 1.35-1.24 (m, 6H), 0.97 (d, J=6.80 Hz, 3H), 0.89 (t, J=7.1 Hz, 3H).

The compound possesses aldehydic, mandarin aldehyde, citrus peel, fruity, floral, and green notes.

Example VII

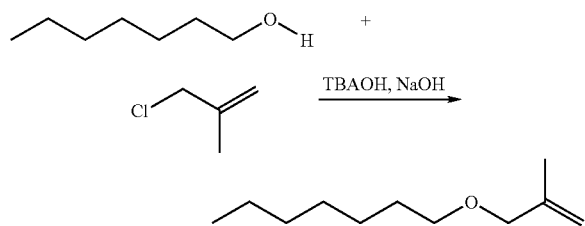

1-(2-methyl-allyloxy)-heptane: In a 3000 mL reaction flask was charged 1-hexanol (400 g, 3.4 mol), a 40% by weight in water solution of tetrabutyl ammonium hydroxide (70 g, 0.11 mol), and a 50% by weight solution of NaOH (296 g, 3.7 mol). The mixture is heated to 70° C. and 3-chloro-2-propene (333 g, 3.7 mol) was fed into the reaction over 3 hours. The reaction was aged for 7 hours at 70° C., and then cooled to room temperature. The reaction is quenched with 600 mL of water and the layers separated. The organic layer washed with 600 mL water and 600 mL of brine. The crude product was purified by distillation to give 415 g of ether, a 71% yield.

1-(2-methyl-allyloxy)-heptane: $^1$H NMR (500 MHz, CDCl$_3$) δ 4.95 (s, 1H), 4.87 (s, 1H), 3.86 (s, 2H), 3.39 (t, J=6.65 Hz, 2H), 1.73 (s, 3H), 1.58 (p, J=7.15 Hz, 2H), 1.37-1.24 (m, 8H), 0.88 (t, J=6.96 Hz, 3H).

The compound possesses herbaceous, green stem, and slightly metallic notes.

Example VIII

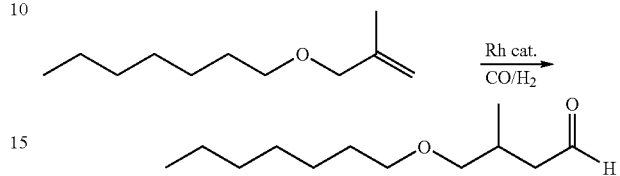

3-methyl-4-heptyloxy-butyraldehyde (IV): To an autoclave was charged Wilkinson's Catalyst catalyst (4.5 g, 4.8 mmol) and 1-(2-methyl-allyloxy)-heptane (390 g, 2.3 mol). The reaction was pressurized to 300 psig with CO/H$_2$, and heated to 112° C. for 3 hours. The reaction was then cooled and returned to atmospheric pressure. The crude material was first rushed over, and then fractionally distilled to yield 306 g of aldehyde 67% yield.

3-methyl-4-heptyloxy-butyraldehyde (IV): $^1$H NMR (500 MHz, CDCl$_3$) δ 9.76 (t, J=2.22 Hz, 1H), 3.40-3.34 (m, 3H), 3.17 (dd, J=9.16, 7.90 Hz, 1H), 2.51 (ddd, J=16.05, 6.37, 2.34 Hz, 1H), 2.37 (octet, J=6.65 Hz, 1H), 2.25 (ddd, J=16.02, 6.90, 2.13 Hz, 1H), 1.53 (p, J=6.98 Hz, 2H), 1.29 (m, 8H), 0.97 (d, J=6.79 Hz, 3H), 0.88 (t, J=6.85 Hz, 3H).

The compound possesses aldehydic, citrus, orange, tangy, juicy, and zesty notes.

Example IX

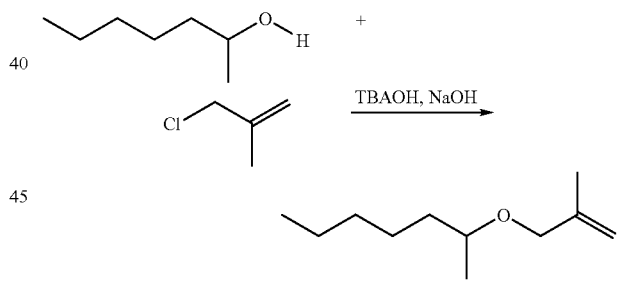

2-(2-methyl-allyloxy)-heptane: In a 3000 mL reaction flask was charged 1-hexanol (625 g, 5.4 mol), a 40% by weight in water solution of tetrabutyl ammonium hydroxide (106 g, 0.16 mol), and a 50% by weight solution of NaOH (460 g, 5.8 mol). The mixture was heated to 70° C. and 3-chloro-2-propene (530 g, 5.8 mol) was fed into the reaction over 3 hours. The reaction was aged for 7 hours at 70° C., and then cooled to room temperature. The reaction was quenched with 800 mL of water, and the layers separated. The organic layer washed with 800 mL water and 800 mL of brine. The crude product was purified by distillation to give 260 g of ether, a 28% yield.

2-(2-methyl-allyloxy)-heptane: $^1$H NMR (500 MHz, CDCl$_3$) δ 4.96 (s, 1H), 4.85 (s, 1H), 3.92 (d, J=8.43 Hz, 1H), 3.82 (d, J=8.44 Hz, 1H), 3.41 (q, J=5.88 Hz, 1H), 1.75 (s, 3H), 1.41-1.26 (m, 8H), 1.13 (d, J=6.10 Hz, 3H), 0.89 (t, J=6.94 Hz, 3H).

The compound possesses green, oily, and cheesy notes.

Example VIII

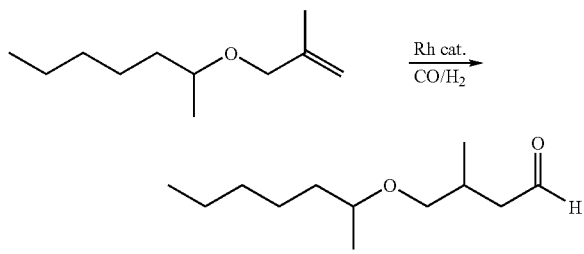

3-Methyl-4-(1-methyl-hexyloxy)-butyraldehyde (V): To an autoclave was charged Wilkinson's Catalyst catalyst (2.8 g, 3.0 mmol) and 2-(2-methyl-allyloxy)-heptane (250 g, 1.5 mol), and 200 mL of methanol. The reaction was pressurized to 300 psig with CO/H$_2$, and heated to 110° C. for 3 hours. The reaction was then cooled and returned to atmospheric pressure. The crude material was first rushed over, and then fractionally distilled to yield 180 g of aldehyde 60% yield.

3-Methyl-4-(1-methyl-hexyloxy)-butyraldehyde (V): $^1$H NMR (500 MHz, CDCl$_3$) δ 9.76 (m, 1H), 3.46-3.41 (m, 0.5H), 3.37-3.28 (m, 1.5H), 3.25-3.20 (m, 0.5H), 3.12-3.07 (m, 0.5H), 2.57-2.47 (m, 1H), 2.38-2.28 (m, 1H), 2.27-2.20 (m, 1H), 1.54-1.45 (m, 1H), 1.39-1.23 (m, 7H), 1.09 (dd, J=5.96, 5.33 Hz, 3H), 0.97 (d, J=6.74 Hz, 3H), 0.89 (t, J=7.07 Hz, 3H).

The compound possesses aldehydic, citrus, lactonic, green and creamy notes.

Example IX

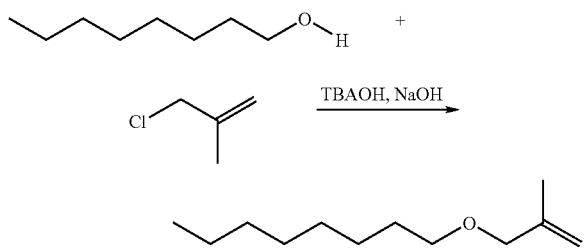

1-(2-methyl-allyloxy)-octane: In a 3000 mL reaction flask was charged 1-hexanol (825 g, 6.3 mol), a 40% by weight in water solution of tetrabutyl ammonium hydroxide (122 g, 0.18 mol), and a 50% by weight solution of NaOH (608 g, 7.6 mol). The mixture was heated to 70° C. and 3-chloro-2-propene (685 g, 7.6 mol) is fed into the reaction over 3.5 hours. The reaction was aged for 7 hours at 70° C., and then cooled to room temperature. The reaction was quenched with 1000 mL of water and the layers separated. The organic layer washed with 1000 mL water and 1000 mL of brine. The crude product was purified by distillation to give 782 g of ether, a 67% yield.

1-(2-methyl-allyloxy)-octane: $^1$H NMR (500 MHz, CDCl$_3$) δ 4.95 (s, 1H), 4.87 (s, 1H), 3.86 (s, 2H), 3.38 (t, J=6.66 Hz, 2H), 1.73 (s, 3H), 1.58 (p, J=7.37 Hz, 2H), 1.37-1.25 (m, 10H), 0.88 (t, J=6.97 Hz, 3H).

The compound possesses chemical, metallic, and cheesy notes.

Example X

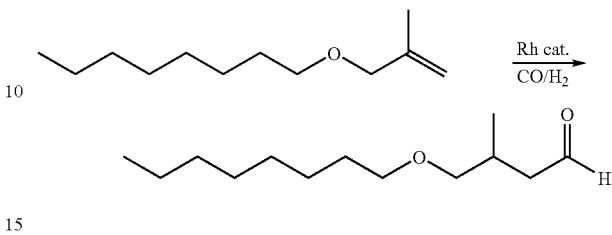

3-Methyl-4-octyloxy-butyraldehyde (VI): To an autoclave was charged Wilkinson's Catalyst catalyst (7.0 g, 7.6 mmol) and 1-(2-methyl-allyloxy)-octane (700 g, 3.8 mol). The reaction was pressurized to 300 psig with CO/H$_2$, and heated to 110° C. for 7 hours. The reaction was then cooled and returned to atmospheric pressure. The crude material was first rushed over, and then fractionally distilled to yield 630 g of aldehyde 77% yield.

3-Methyl-4-octyloxy-butyraldehyde (VI): $^1$H NMR (500 MHz, CDCl$_3$) δ 9.76 (s, 1H), 3.41-3.33 (m, 3H), 3.17 (t, J=8.63, 1H), 2.51 (ddd, J=6.33, 6.32, 1.9 Hz, 1H), 2.37 (octet, J=6.59 Hz, 1H), 2.25 (ddd, J=7.43, 6.87, 1.72 Hz, 1H), 1.53 (p, J=6.85 Hz, 2H), 1.28 (s, 10H), 0.97 (d, J=6.79 Hz, 3H), 0.88 (t, J=6.71 Hz, 3H).

The compound possesses aldehydic, fatty, and citrus notes.

Example XI

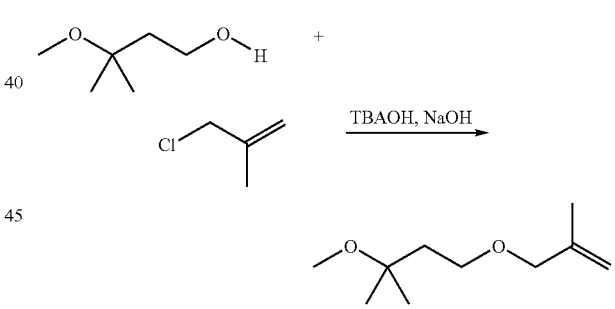

1-(2-methyl-allyloxy)-3-methoxy-3-methyl-1-butane: In a 3000 mL reaction flask was charged 3-methoxy-3-methyl-1-butanol (472 g, 4.0 mol), a 40% by weight in water solution of tetrabutyl ammonium hydroxide (100 g, 0.15 mol), and a 50% by weight solution of NaOH (366 g, 4.6 mol). The mixture was heated to 70° C. and 3-chloro-2-propene (420 g, 4.6 mol) was fed into the reaction over 3 hours. The reaction was aged for 7 hours at 70° C., and then cooled to room temperature. The reaction was quenched with 600 mL of water, and the layers separated. The organic layer washed with 600 mL water and 600 mL of brine. The crude product was purified by distillation to give 420 g of ether, a 61% yield.

1-(2-methyl-allyloxy)-3-methoxy-3-methyl-1-butane: $^1$H NMR (500 MHz, CDCl$_3$) δ 4.95 (s, 1H), 4.88 (s, 1H), 3.86 (s, 2H), 3.49 (t, J=7.28 Hz, 2H), 3.19 (s, 3H), 1.82 (t, J=7.28 Hz, 2H), 1.74 (s, 3H), 1.18 (s, 6H).

The compound possesses fresh, floral, fruity, linalool, and green notes.

Example XII

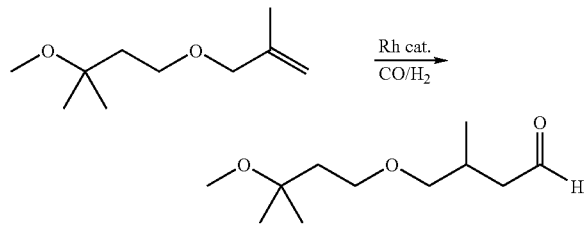

3-Methyl-4-(3-methly-3-methoxy butyloxy)-butyraldehyde (VII): To an autoclave was charged Wilkinson's Catalyst catalyst (4.5 g, 4.8 mmol) and 1-(2-methyl-allyloxy)-octane (414 g, 2.4 mol). The reaction was pressurized to 300 psig with $CO/H_2$, and heated to 110° C. for 5 hours. The reaction was then cooled and returned to atmospheric pressure. The crude material was first rushed over, and then fractionally distilled to yield 376 g of aldehyde 77% yield.

3-Methyl-4-(3-methly-3-methoxy-butyloxy)-butyraldehyde (VII): $^1$H NMR (500 MHz, $CDCl_3$) δ 9.75 (t, J=1.85 Hz, 1H), 3.52-3.41 (m, 2H), 3.38-3.33 (m, 1H), 3.20-3.16 (m, 1H), 3.18 (s, 3H), 2.53-2.46 (ddd, J=16.03, 6.32, 2.1 Hz, 1H), 2.41-2.31 (sextet, J=6.77 Hz, 1H), 2.21-2.19 (ddd, J=16.02, 6.83, 1.91 Hz, 1H), 1.76 (t, J=7.17 Hz, 2H), 1.16 (s, 6H), 0.97 (d, J=6.78 Hz, 3H).

The compound possesses aldehydic, fatty, and citrus notes.

We claim:

1. 3-methyl-4-heptyloxy-butyraldehyde.

2. A fragrance formulation containing an olfactory effective amount of methyl-4-heptyloxy-butyraldehyde.

3. A fragrance product selected from the group consisting of soaps, shower gels, hair care products, air fresheners, cosmetic preparations, detergents, dishwashing materials, scrubbing compositions, and window cleaners, said fragrance product containing 3-methyl-4-heptyloxy-butyraldehyde.

* * * * *